United States Patent [19]

Bull et al.

[11] Patent Number: 4,619,827
[45] Date of Patent: Oct. 28, 1986

[54] METHOD FOR ADMINISTERING EQUINE VACCINES AND COMPOSITIONS THEREFOR

[75] Inventors: Robert W. Bull, Haslett; Robert M. Soltysiak; Paul D. Minnick, both of East Lansing, all of Mich.

[73] Assignee: Neogen Corporation, Lansing, Mich.

[21] Appl. No.: 785,001

[22] Filed: Oct. 7, 1985

[51] Int. Cl.$^4$ .................... A61K 39/12; A61K 45/02
[52] U.S. Cl. ........................ 424/89; 424/85; 424/86; 424/88
[58] Field of Search .................. 424/89, 92, 88, 85, 424/86

[56] References Cited

U.S. PATENT DOCUMENTS

| | | | |
|---|---|---|---|
| 3,518,347 | 6/1970 | Pavilanis et al. | 424/89 |
| 3,699,222 | 10/1972 | Isaacs et al. | 424/85 |
| 3,790,665 | 2/1974 | Carlson et al. | |
| 3,793,150 | 2/1974 | Usdin | 424/92 X |
| 3,906,092 | 9/1975 | Hilleman et al. | 424/89 |
| 3,919,411 | 11/1975 | Glass et al. | |
| 3,970,749 | 7/1976 | Baugh | 424/85 X |
| 4,009,258 | 2/1977 | Kilbourne | 424/89 |
| 4,466,957 | 8/1984 | Hjorth et al. | 424/89 |
| 4,503,035 | 3/1985 | Pestka et al. | 424/85 |

OTHER PUBLICATIONS

Litvinov, Chem. Abstracts, 67, 7536,80070u, 1967.
Antibiotiki, 12(7), 602-604 (1967), Litvinov.
Iscove, N. N., et al., J. Exp Med. 147: 923-933 (1978).
Langford et al., Methods in Enzymology, vol. 78, Academic Press, N.Y., N.Y., p. 339, (1981).
Hierholzer, J.C. et al., Appl. Microbiol. 18:824-833 (1969).

*Primary Examiner*—Howard E. Schain
*Attorney, Agent, or Firm*—Ian C. McLeod

[57] ABSTRACT

A method for enhancing a vaccine immune response in equines using leukokines, particularly mixed leucokines, is described. The leukokines can be administered separately or admixed with the vaccine. The method and vaccine compositions are particularly effective where equine influenza vaccine and mixed leukokines are administered together to the equine.

17 Claims, 4 Drawing Figures

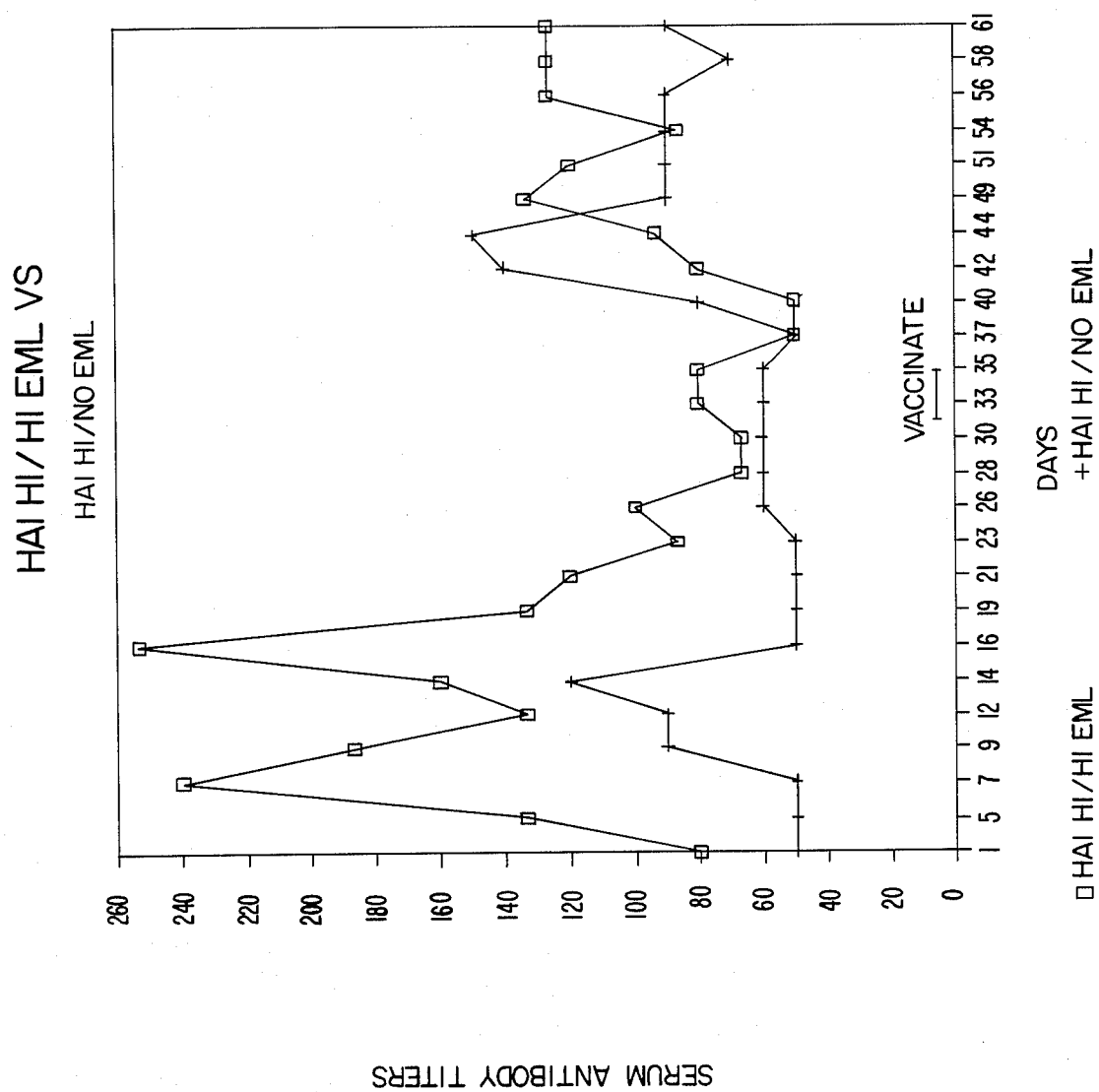

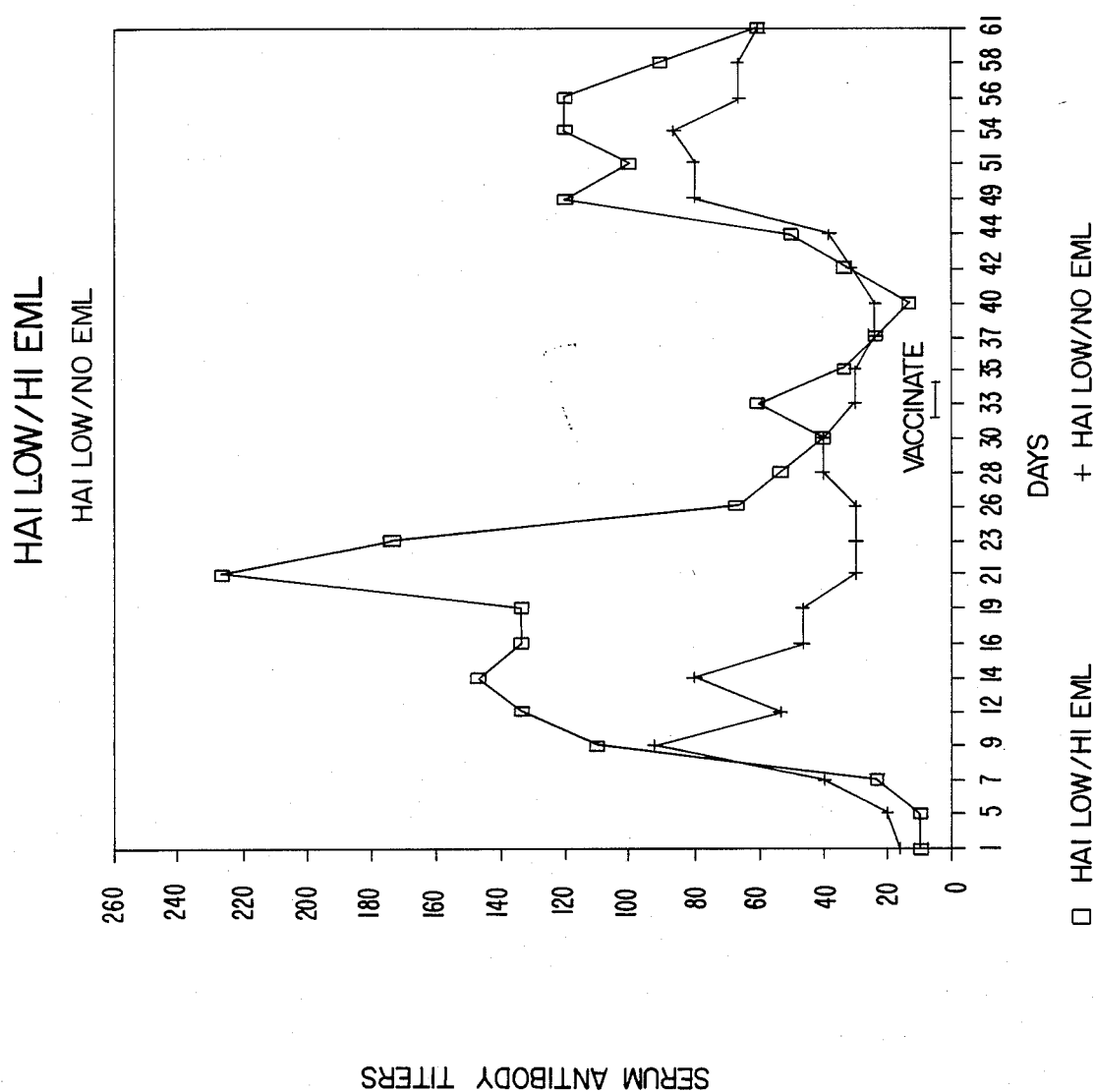

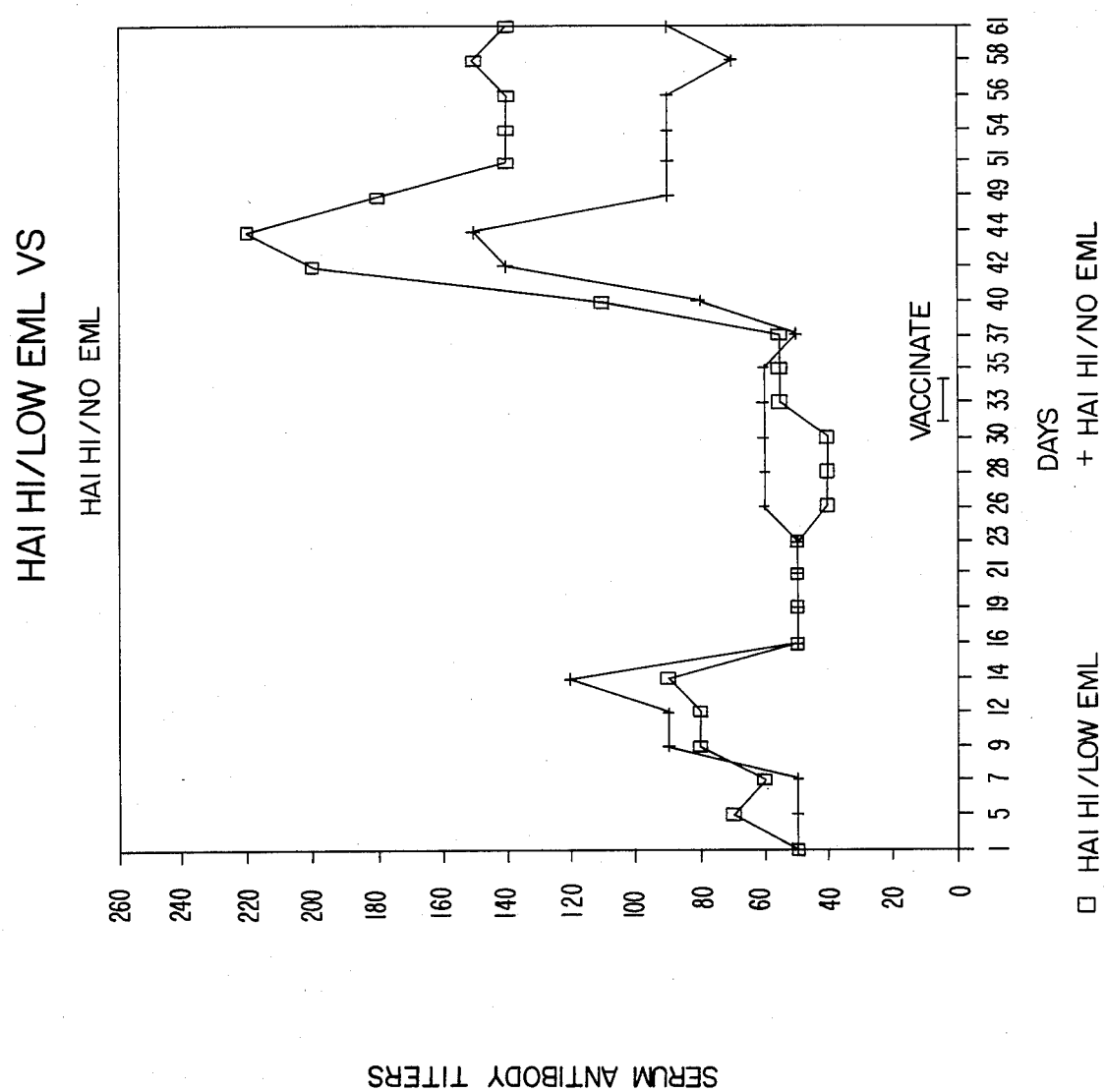

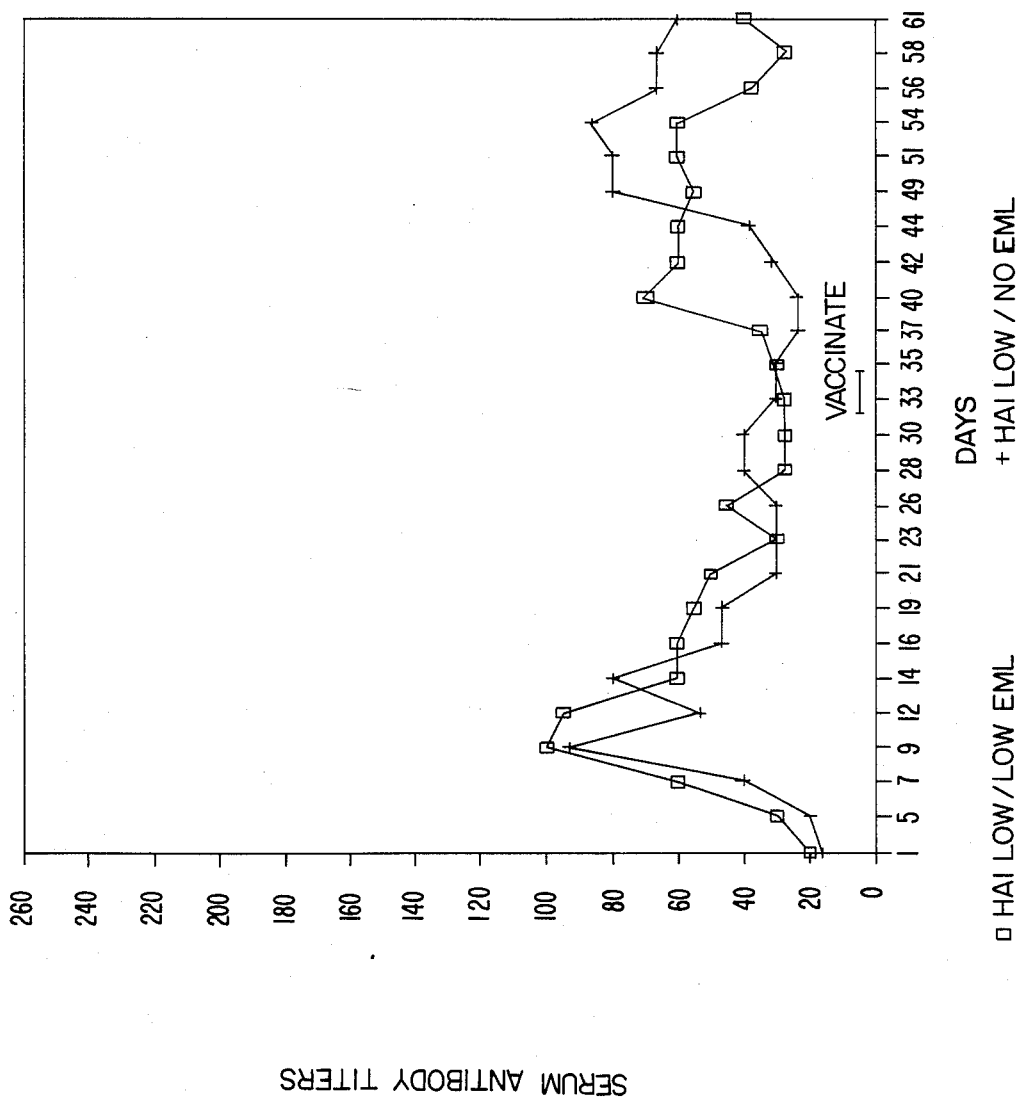

METHOD FOR ADMINISTERING EQUINE VACCINES AND COMPOSITIONS THEREFOR

BACKGROUND OF THE INVENTION (1) Field of the Invention

The present invention relates to an equine vaccination method wherein the vaccine is potentiated by a leukokine or mixed leukokines administered with the vaccine. In particular, the present invention relates to the potentiation of an equine influenza vaccine with mixed equine leukokines.

(2) Prior Art

The prior art relating to interferon is extensive. U.S. Pat. No. 3,699,222 (1972) to Isaacs and Lindenmann describes the original research with interferon as an antiviral agent. U.S. Pat. No. 4,503,035 (1985) to Pestka and Rubinstein describes purified interferons and in particular the use of leukocytes and a virus (Newcastle Disease virus) for inducing the interferons. Example 7 of this patent particularly describes the use of this procedure to produce equine interferbn.

The term "interferon" is generally used by the prior art to refer to induced proteins of leucocyte and of fibroblast origins which interfere with viral replication. The terms "leukokine" or "leucokine" have been used in the recent literature to characterize proteins including interferons of leukocyte origins and the term leukokine is used herein.

The presence of interferons in the blood stream with virus vaccines is known to increase or enhance the immune antibody response. U.S. Pat. No. 3,906,092 to Hilleman, Tytell and Woodhour (1975) describes the use of interferon inducing polynucleotides as adjuvants to non-replicating (killed virus) vaccines to enhance antibody formation. The administration of mixed live Newcastle disease virus vaccine and interferon to provide an enhanced protection for chickens is described as prior art in this patent, but there is no description of the administration of interferon and a non-replicating virus vaccine. It is not believed that the use of interferons with equine vaccines has been described by the prior art.

Vaccination with commercially available inactivated equine influenza virus vaccine alone (consisting of killed virus of tissue culture origin) produces a variable humoral immune antibody response in equines. This variation is in the magnitude of the antibody response, the time course in which the equine responds to the vaccine, and the duration of the antibody response. These variations have been recognized and accepted as due to biological variation of the species' immune system. Where there is an urgent need for immunity, the equine is repeatedly vaccinated with influenza vaccine.

New and more potent vaccines which augment the equine's immune response to influenza or other viral vaccine vaccination and thereby greatly increase both the likelihood and extent of a protected period with less frequent vaccination, are needed. Further, vaccines are needed where there is a less variable response to the vaccination.

OBJECTS

It is therefore an object of the present invention to provide improved vaccine compositions containing an admixture of an equine replicating or non-replicating virus vaccine and of a leukokine as an adjuvant, wherein there is an increased antibody response from use of the composition in the equines. Further it is an object of the present invention to provide a method for administering the vaccine with the leukokine which provides the improved response. It is particularly an object of the present invention to provide an improved method and vaccine compositions for providing immunity to equine influenza. These and other objects will become increasingly apparent by reference to the following description and the drawings.

IN THE DRAWINGS

FIG. 1 is a graph of serum antibody response in equines to separate and concurrent coadministered injections of bivalent equine influenza vaccine (Haver-Lockhart Labs, Shawnee, Kansas) (combined Miami and Prague strains) (1) Equi-1 and Equi-2 with a level of equine leukokines of 200,000 International Antiviral Units, (IU) or (2) with no leukokines. The equines had a high initial serum antibody titer of 1:60 or higher to A/Equi-2/Miami/1/63 which appears to indicate some level of immunity most likely as a result of prior exposure to influenza virus.

FIG. 2 is a graph showing the same separate and concurrent coadministration as in the graph FIG. 1, i.e. (1) (200,000 IU) or (2) no leukokines, except that the equines had a low initial antibody titer of 1:20 or less.

FIG. 3 is a graph showing the same separate and concurrent coadministration as in the graph FIG. 1, except that (1) the leukokines were coadministered with the vaccine at a low level (20,000 IU) or (2) no leukokines were administered with the vaccine. The equines initially had a high level of serum antibody of 1:60 or higher.

FIG. 4 is a graph showing the same coadministration as in the graph FIG. 2, except that the leukokines were coadministered (1) at a low level (20,000 IU) or (2) no leukokine was administered. The equines initially had a low level of serum antibody of 1:20 or less.

GENERAL DESCRIPTION

The present invention relates to an improvement in a method for providing an immune response to an equine disease with a viral or viral subunit or other antigen vaccine which produces a blood serum antibody response to the vaccine in the equine which comprises: administering an equine leukokine with the vaccine to thereby provide an enhanced immune response in the equine. The method particularly relates to the treatment of equine influenza.

Further the present invention relates to a vaccine composition for an equine which comprises in admixture: a viral or viral subunit or other antigen vaccine which produces a blood serum antibody response to the vaccine in the equine to provide an immune response to a viral disease; and an equine leukokine as an adjuvant to the vaccine, wherein the leukokine is present in an amount which increases the blood serum antibody response to the vaccine in the equine. The leukokine generally substantially increases the initial antibody response in the equines.

The leukokines induced by the virus without purification is mixed with other leukokines of differing molecular size and no attempt is made to purify the leukokines because of the expense; however, this can be done in the manner of U.S. Pat. No. 4,503,035. It is expected that the purified leukokines administered with the vaccine would individually produce more or less antibody response in the equine.

The most practical method of producing the leukokines is by virus induction of equine leukocytes in vitro. The preferred virus produces Newcastle disease in chickens. Other viruses which can be used, for instance, are Bluetongue virus, Sindbis virus and Sendai virus. It is generally impractical to isolate the leukokines in vivo. Recombinant genetic techniques can be used to produce the leukokines in bacteria.

The viral, viral subunit or other antigen vaccines are very well known to those skilled in the art. It is especially unexpected that the leukokines would enhance the serum antibody of non-replicating vaccines, such as the equine influenza virus vaccines. The virus are killed by formalin in producing the equine influenza vaccine used in the preferred compositions and method of the present invention.

Examples of vaccines where the antibody response in equines can be enhanced are those intended for prophylaxis of viral arteritis; equine encephalomyelitis (Eastern, Western Encephalitis, equine sleeping sickness); equine rhinopneumonitis (herpesvirus type 1); equine abortion (herpesvirus type 3); African horse sickness; and foal gastroenteritis (equine rotavirus).

The vaccine compositions can be administered to the equines in any convenient manner. The most common means is by injection, although nasal sprays and other techniques for blood stream absorption vaccines can be used. The vaccines can be separately administered or administered together. The vaccine dosages are usually administered in dosages of 1 ml, usually 0.1 to 5 ml intramuscularly.

The vaccine compositions used are well known to those skilled in the art. U.S. Pat. No. 4,466,957 to Hjorth et al, U.S. Pat. Nos. 4,009,258 and 3,518,347, for instance, describe influenza vaccines.

The vaccines can include other conventional adjuvants. These include complete or incomplete Freund's, aluminum hydroxide, peanut oil, by way of example. U.S. Pat. Nos. 3,790,655 and 3,919,411 to Carlson et al describe adjuvants used in the vaccines used in the specific examples.

Preferably the dosage of the leukokine used with the vaccine is between about 20,000 and 1,000,000 International Units. The assay for the leukokines used in the present invention uses a human interferon preparation developed by the National Institute of Health as a reference standard as discussed herein.

In particular, equine mixed leukokines (EML), when adinistered separately intramuscularly along with a formalin-inactivated combined equine (influenza) virus vaccine, cause an increase of humoral immune antibody response to the vaccine antigen in equines. The EML are produced by induction of isolated equine leukocytes with Newcastle Disease Virus in vitro. The EML were extracted and partially purified by diafiltration and ultrafiltration but the induced leukokines are not isolated. The increase in antibodies reactive with the vaccine antigens occurs more rapidly and is of greater magnitude with the leukokines than the antibody response from the vaccine alone. This translates to a greater assurance of protection against equine (influenza) virus, with the resultant economic and practical benefits of realizing that protection from fewer vaccinations.

SPECIFIC DESCRIPTION

A. Process of Producing Equine Mixed Leukokines (EML).

1. Collection and Preparation of Equine Leukocytes.

a. Equine peripheral blood leukocytes were collected by a process of leukophoresis in which up to 10 L of peripheral blood from a single animal were subjected to processing. The peripheral blood leukocytes were retained and the red blood cells and plasma returned to the animal.

b. The volume of the peripheral blood leukocytes obtained was assessed in an appropriate vessel and the cells were diluted to a volume three times the starting volume with cold Tris-HCl buffered ammonium chloride (140 mM NH$_4$Cl, 6mM Tris-HCl), pH 7.4, to initiate the elimination of any remaining red blood cells.

c. After five minutes incubation at room temperature, with frequent agitation, the cell suspension was centrifuged at 500×g for 15 minutes at 4 degrees Centigrade.

d. The cell pellet was resuspended in a minimal amount of Hank's Balanced Salt Solution without Ca$^{2+}$ and Mg$^{2+}$ (HBSS), pH 7.4, and centrifuged at 500×g for 15 minutes at 4° C.

e. Following a subsequent wash with HBSS, pH 7.4, the cells were resuspended in a known volume of HBSS.

f. A portion of the cell suspension was diluted 1:20 with HBSS and the total number of cells estimated by hemocytometer count.

g. Cells in the original suspension were pelleted by centrifugation at 500×g for 15 minutes at 4 degrees C. and resuspended in nutrient medium to result in a final concentration of 1×10 (7) cells /ml.

2. Preparation of Newcastle Disease Virus (NDV) for Induction, and Determination of Hemagglutination Titer.

a. NDV (strain Bl, Hitchner; ATTC VR-108) was inoculated into the allantoic cavity of 10 day embryonated eggs, and allantoic fluid containing virus was harvested after a further 72 hour incubation. The allantoic fluids were pooled so as to result in several lots.

b. Freshly drawn chicken blood was mixed 1:1 with cold Alsever's solution (0.42% NaCl, 0.8% trisodium citrate, 2.05% glucose, 0.055% citric acid, pH 7.4) and centrifuged at 500×g for 15 minutes.

c. Serum and Alsever's solution were decanted and discarded.

d. Cells were resuspended in Alsever's solution, mixed thoroughly, and centrifuged at 500×g for 15 minutes.

e. Resuspension of cells, centrifugation, and decantation were repeated.

f. From the packed cell volume, a 0.5% suspension of the chick red blood cells (CRBC) was made in PBS.

g. To each of twelve (12) consecutive wells of a 96 well microtiter plate (v-shaped wells) was added 0.1 ml PBS.

h. 0.1 ml of allantoic fluid from a single lot was added to the first well.

i. Serial 2-fold dilutions were made by transferring 0.1 ml of each consecutive dilution out through well 12.

j. 0.1 ml of the 0.5% CRBC suspension was added to each well.

k. The above procedure was followed for every lot of NDV-containing allantoic fluid in the current pool.

l. 0.1 ml of the 0.5% CRBC suspension was added to 3 wells containing only 0.1 ml PBS (negative control wells).

m. Hemagglutination was assessed when CRBC's in the control wells form "buttons" in the bottom of the wells (the "buttons" ran when the plate was slightly tilted). The titer was equal to the reciprocal of the highest dilution which interferes with "button" formation of the control type, expressed in hemagglutinating units/ml (HAU/ml).

n. Individual lots from the current pool of allantoic fluid which showed the highest HAU/ml were pooled for induction.

o. The induction pool was dispensed such that each aliquot contains enough NDV for 3 to 5 liters of nutrient induction medium, based on a final 15 HAU/ml. Aliquots were stored at −70 degrees Centigrade until use.

3. Preparation of Nutrient Medium for Leukocyte Culture.

a. The nutrient medium for maintenance of the isolated equine peripheral blood leukocytes in which the cells were induced to produce EML, was similar to that described by N. N. Iscove and F. Melchers. (J. Exp. Med 147:923–933, 1978), with the modifications specified below:

1. Iscove's Modification of Dulbecco's Modified Eagle's Medium (IDMEM; Gibco, Grand Island, N.Y.) was rehydrated according to package directions.

2. Addition was made of alpha-thioglycerol (Sigma, St. Louis, MO.) to a concentration of 75 mcM, in nutrient medium.

3. An emulsion of soybean lecithin (type II-S; Sigma) was made in 100 ml of Dulbecco's Modified Eagle's Medium (DMEM) also containing 10 mg/ml fatty acid-free bovine serum albumin (FAF-BSA; Sigma), pH 5.0, by trituration and homogenization of 750 mg of lecithin and including it in the final 10 ml of DMEM--BSA. This mixture was filtered through a sterile 0.45 micron membrane (Millipore) before addition to the nutrient medium to achieve the final concentrations of lecithin (75 mcg/ml) and BSA (100 mcg/ml).

4. Fetuin (Spiro method; Gibco) was added to the nutrient medium to achieve final concentration of 150 mcg/ml.

5. Transferrin (Gibco), 4 mg/ml was ⅓ saturated by the addition of 296 nmol Fe(NO$_3$)$_3$, passed through a 0.2 micron filter (Millipore, Bedford, MA), and added to the nutrient medium to a final transferrin concentration of 1 mcg/ml.

4. Induction of Equine Leukocytes for Production, and Recovery of the EML.

a. The washed equine leukocytes were suspended in the complete nutrient medium at a final concentration of $1 \times 10^7$ cells/ml in the induction vessel (BioCul Type 20 Cell Culture System; Queue Systems, Parkersburg W.V.). To this cell suspension were added EML, previously induced, purified and concentrated by this procedure, to a final concentration of 50 antiviral units/ml of nutrient medium.

b. The contents of the induction vessel were gently stirred in a constant temperature waterbath (37° C.) for 5 hours. During this and the subsequent incubation, the pH was monitored by an internal probe and adjusted to pH 7.4 by automatic addition of acid or base.

c. After 5 hours of incubation, allantoic fluid grown Newcastle Disease Virus (NDV) was added to a final concentration of 15 HAU/ml. The HAU of the NDV pool had previously been assayed by standard methods (Sec. 2 above).

d. Incubation was continued for 18 to 20 hours at 37° and pH 7.4 with gentle stirring to maintain the cells in suspension.

e. The contents of the induction vessel were transferred aseptically to sterile centrifuge bottles and centrifuged at $1500 \times g$ 30 minutes at 4° C. The cell pellet was discarded.

f. A sample of the supernatant was taken for centrifugation at $100,000 \times g$ for 1 hour before assay for antiviral activity by the plaque reduction method described hereinafter. The balance was held at −20° C. until processing.

5. Diafiltration, Ultrafiltration and Concentration of EML.

a. Supernatant collected from the induction vessel was diafiltered using an Amicon DC 10L ultrafiltration unit fitted with a 100,000 MW cut-off hollow fiber cartridge (H5P100-43; Amicon Corp., Danvers, MA). Prior to diafiltration the cartridge was cleaned and equilibrated by sequentially running through the unit:

1. Five liters of 0.2 M NaOH for 20 minutes,

2. Five liters of distilled H$_2$O for 2 rinses of 20 minutes each,

3. Two liters of phosphate buffered saline (0.8% NaCl, 0.02% KCl, 0.12% Na$_2$HPO$_4$, 0.02% KH$_2$PO$_4$; PBS), pH 9.0, containing 0.5% fraction V albumin, for 20 minutes, 4. Two liters of 5 mM sodium phosphate buffer, pH 7.4, for 20 minutes.

After loading the supernatant, diafiltration was initiated with 6 to 7 volumes of 5 mM sodium phosphate buffer, pH 7.4, which resulted in reduction of the reservoir volume to approximately 500 ml. Samples were removed for assay of antiviral activity and to determine absence or presence of live virus.

b. Following decontamination of the ultrafiltration unit by a 20 minute rinse with 5 L of 0.2 N NaOH, it was next fitted with a hollow-fiber cartridge with a 10,000 MW cut-off limit (H10P10-20) and steps 1) through 4) of 4.a. above were repeated.

c. The diafiltrate was ultrafiltered and concentrated against the 10,000 MW hollow fiber cartridge to approximately 500 ml.

d. The remaining crude EML product was removed from the reservoir, filter sterilized by use of a 0.2 micron filter apparatus (Millipore), distributed to sterile vials, and lyophilized.

e. Contents of random vials were taken for assessment of sterility, antiviral activity, protein content, and other biochemical characterizations.

6. Plaque Assay for Antiviral Activity of EML.

a. Virus plaque reduction assay was performed as described by Langford, et al. (Methods in Enzymology, V. 78, Academic Press, New York, N.Y., p. 339, 1981), utilizing monolayers of equine dermal fibroblasts (E. Derm, ATCC-CCL57) challenged with Vesicular Stomatitis virus.

b. In this assay, utilizing WISH human amniotic cells, NIH Reference Human Interferon Alpha (HuIFN-alpha[Leukocyte/Sendai]Ga23-902-530), having an assigned potency of 4.08 log 10 International Units (IU)/ml, demonstrates 4.59 log10IU/ml.

B. Use of EML to Augment the Humoral Immune Response to Commercially Available Killed Equine Influenza Virus Vaccine 1. The EML, produced as described above, were reconstituted from the lyophilized state with sterile distilled water so as to result in an injection volume of 1 to 5 ml containing 20,000 to 200,000 units of antiviral activity for intramuscular administration to the animals.

2. At the time of vaccination with the commercially available formalin-inactivated equine influenza virus vaccine, the EML were separately co-administered by intramuscular injection. Subcutaneous injection could also have been used.

3. Humoral antibody responses of animals after injection with the vaccine alone or with EML injection were assessed by standard hemagglutination inhibition (HAI) tests as modified from Hierholzer, J.C., Suggs, M. T, and Hall, E. C. (Appl. Microbiol. 18:824–833, 1969) as adapted for the microtiter method, using as antigen allantoic fluid-grown influenza viruses of the same prototype strains as used in the equine vaccine (currently these are A/equi-2/Miami/1/63 and A/equi-2/Prague/1/56).

a. Equine sera for assay were pretreated and diluted as follows:

1. To 0.5 ml serum was added 2.0 ml borate-buffered saline (0.7% NaCl, 0.3% $H_3BO_3$, 0.01% NaOH; BBS), pH 9.0, and 2.5 ml of a 25% suspension of acid-washed kaolin (Sigma) in BBS, pH 9.0.

2. The solution was shaken vigorously at 5 minute intervals for 20 minutes at 24 degrees Centigrade.

3. The solution was centrifuged at 800×g for 30 minutes.

4. The supernatant was decanted to separate tubes. This represents a 1:10 dilution of original serum.

5. The diluted serum was inactivated at 56 degrees Centigrade for 30 minutes.

b. The hemagglutination inhibition (HAI) test was run as follows using 96 well microtiter trays:

1. 25 mcl PBS was added to wells 2 through 12 of rows designated for serum dilutions.

2. 50 mcl PBS was added to 3 wells for cell controls, and to 6 others for virus "back-titration".

3. 50 mcl of each of the starting serum dilutions (1:10) was added to the first wells of each of two rows in which serum dilutions will be made.

4. Serial 2-fold dilutions of the sera by transfer of 25 mcl were made to each well out through well 12 of each row.

5. 25 mcl of PBS was added to all wells of every second row (these were serum control wells).

6. The appropriate allantoic fluid-grown influenza virus in PBS were diluted such that 0.1 ml contains 16 HAU of activity (Sec. 8.A.2., determination of HAU).

7. 25 mcl (4 HAU) of the virus dilution were added to all wells of the remaining rows which contain serum dilutions (these are the serum-antigen wells).

8. 50 mcl of the virus dilution were added to the first of the wells for antigen "back-titration".

9. Further serial 2-fold dilutions of the virus dilution were made by transfer of 50 mcl to each well through well 6.

10. The plates were shaken carefully and incubate at 24 degrees Centigrade for 30 minutes.

11. 50 mcl of a 0.5% suspension of CRBC's (Sec. 8.A.2.b-f) were added to all wells.

12. The plates were shaken carefully, and incubation continued.

13. The plates were read for HAI when the cell control wells showed compact "buttons". Cell control "buttons" ran when the plate was tilted, as should any HAI-positive wells (those where hemagglutination had been inhibited by antibody). HAI-negative wells show an even distribution of CRBC over the bottom of the wells. The HAI titer of the serum was expressed as the reciprocal of the serum dilution (starting dilution is 1:10) in the last well to show a "button" (no hemagglutination).

14. Serum control wells should not show hemagglutination (auto-agglutination); any auto-agglutination may mask low serum antibody titers.

15. Virus "back-titration" should indicate the presence of 4 HAU/25 mcl. Typically, the first 3 wells will show hemagglutination, the last 3 wells will "button".

At the time of vaccination of an equine with killed equine influenza virus vaccine, 20,000 to 1,000,000 units of EML was also administered intramuscularly, preferably 200,000 to 400,000 units. FIGS. 1 to 4 show the results of the vaccination. The results are quite pronounced where the equines had higher levels of the antiflu antibody initially. Administration of higher levels of leukokines also produced improved results. As shown in the Figures the equines were revaccinated at day 31 to 34. The influenza vaccine was in a dosage of 1 ml.

FIGS. 1 to 4 show vaccinations as follows:

HAI LO Group: serum titer 1:20 or less to A/Equi-2/Miami/1/63 at start of study.

Vaccinate+EML (200,000 IU antiviral activity)
Vaccinate+EML (20,000 IU antiviral activity)
Vaccinate−no EML (control group)

HAI HI Group: serum titer 1:60 or higher to A/Equi-2/Miami/1/63 at start of study)

Vaccinate+EML (200,000 IU antiviral activity)
Vaccinate+EML (20,000 IU antiviral activity)
Vaccinate−no EML (control group)

Three equines were used per group. The EML equines receive EML on two occasions (when vaccinated). Blood is drawn every second day for about 70 days. All equines received the second vaccination with-/without EML on approximately day 33. Serum anti-flu titer in FIGS. 1 to 4 refers to the reciprocal of the serum dilution resulting in inhibition of erythrocyte agglutination.

As can be seen from the foregoing specific description the EML of the present invention are very effective in increasing the serum antibody titer for equine influenza vaccine. Similar effects can be expected with other vaccines since the results should not depend upon a particular vaccine antigen.

We claim:

1. In a method for providing an immune response to an equine disease with a viral or viral subunit or other viral-derived antigen vaccine which produces a blood serum improvement which comprises:

administering an equine leukokine with the vaccine to thereby provide an enhanced immune response in the equine.

2. The method of claim 1 wherein the vaccine and leukokine are administered in admixture to the equine.

3. The method of claim 1 wherein prior to administration the leukokine has been induced by a virus in a medium containing leucocytes and then separated from the medium and leucocytes.

4. The method of claim 3 wherein the virus which induced the leukokine produces Newcastles disease in chickens.

5. The method of claim 1 wherein the vaccine is for equine influenza.

6. The method of claim 5 wherein between about 20,000 and 1,000,000 International Antiviral Units of the leukokine are administered to the equine with the vaccine.

7. The method of claim 1 wherein the leukokine and vaccine are administered separately and concurrently.

8. The method of claim 1 wherein the vaccine and leukokines are administered by injection.

9. The method of claim 1 wherein the administration is by injection, wherein the vaccine and leukokine are administered separately and concurrently and wherein the leukokine is induced in the leucocytes by a virus which produces Newcastles disease in chickens.

10. The method of claim 1 wherein the leukokine is an admixture of leukokines of different molecular size.

11. A vaccine composition for an equine which comprises in admixture:
(a) a viral or viral subunit or other viral-derived antigen vaccine which produces a blood serum antibody response to the vaccine in the equine to provide an immune response to a viral disease; and
(b) an equine leukokine as an adjuvant to the vaccine, wherein the leukokine is present with the vaccine in a dosage of 0.1 to 5 ml of the composition in an amount which increases the blood serum antibody response to the vaccine in the equine when administered intramuscularly.

12. The vaccine composition of claim 11 wherein the leukokine prior to admixture has been induced by a virus in a medium containing leucocytes and then separated from the medium.

13. The vaccine composition of claim 12 wherein the virus which induced the leukokine produces Newcastles disease in chickens.

14. The vaccine composition of claim 11 wherein the leukokines are a mixture of leukokines of different molecular size.

15. An influenza vaccine composition for an equine which comprises in admixture:
(a) a viral influenza vaccine which produces a blood serum antibody response to the vaccine in the equine to provide equine influenza immunity; and
(b) an equine leukokine as an adjuvant to the vaccine, wherein the leukokine is present with the vaccine in a dosage of 0.1 to 5 ml of the composition in an amount which increases the blood serum antibody response to the vaccine in the equine when administrated intramuscularly.

16. The vaccine composition of claim 15 wherein between about 20,000 and 100,000 Internation Antiviral Units of the leukokines in the vaccine are administered.

17. The vaccine composition of claim 16 wherein the vaccine is administered in a dosage between about 0.1 to 5 ml.

* * * * *

UNITED STATES PATENT AND TRADEMARK OFFICE
CERTIFICATE OF CORRECTION

PATENT NO. : 4,619,827

DATED : October 28, 1986

INVENTOR(S) : Robert W. Bull, Robert M. Soltysiak and
Paul D. Minnick

It is certified that error appears in the above-identified patent and that said Letters Patent are hereby corrected as shown below:

Column 1, line 22, "interferbn" should be --interferon--.

Column 3, line 53 "adinistered" should be --administered--.

Column 8, line 59, after "serum" insert the following --antibody response to the vaccine in the equine the--.

Column 10, line 25 "100,000 Internation" should be --1,000,000 International--.

Column 10, line 28 "0.1 to 5 ml." should be --0.1 and 5 ml.--.

Signed and Sealed this

Fourteenth Day of April, 1987

*Attest:*

DONALD J. QUIGG

*Attesting Officer*  *Commissioner of Patents and Trademarks*